United States Patent [19]
Sher

[11] Patent Number: 5,769,172
[45] Date of Patent: Jun. 23, 1998

[54] POWER TOOL

[76] Inventor: Arieh Sher, 35 Spinoza Street, Rehovot, 76452, Israel

[21] Appl. No.: 693,782

[22] Filed: Jul. 22, 1996

Related U.S. Application Data

[63] Continuation-in-part of Ser. No. 473,880, Jun. 7, 1995, Pat. No. 5,592,866, which is a continuation of Ser. No. 100,949, Aug. 3, 1993, Pat. No. 5,467,684, which is a continuation-in-part of Ser. No. 83,760, Jun. 30, 1993, Pat. No. 5,350,390, which is a continuation of Ser. No. 857,556, Mar. 25, 1992, abandoned.

[51] Int. Cl.$^6$ .................................................. B25D 16/00
[52] U.S. Cl. ............................................. 173/97; 173/111
[58] Field of Search ................................. 173/97, 94, 95, 173/110, 111, 109; 74/128

[56] References Cited

U.S. PATENT DOCUMENTS

| | | | |
|---|---|---|---|
| 2,558,165 | 6/1951 | Anderson | 173/111 |
| 3,171,501 | 3/1965 | Lear | 173/97 |
| 3,323,601 | 6/1967 | Uebel | 173/97 |
| 3,404,739 | 10/1968 | Worman | 173/111 |
| 4,359,109 | 11/1982 | Truong-Cao | 173/111 |
| 4,745,980 | 5/1988 | Chung | 173/111 |

*Primary Examiner*—Scott A. Smith

[57] ABSTRACT

A bi-directional power tool for driving fasteners and for drilling purposes. The power tool comprises a rotary piston driving mechanism and a linear sliding member that transform a longitudinal motion of a piston in a cylinder to a rotation movement of a working head. The power tool includes a driving unit that comprises a pressure generator and a controller that controls the operation of the tool. Alternatively the power tool can be operated manually.

14 Claims, 4 Drawing Sheets

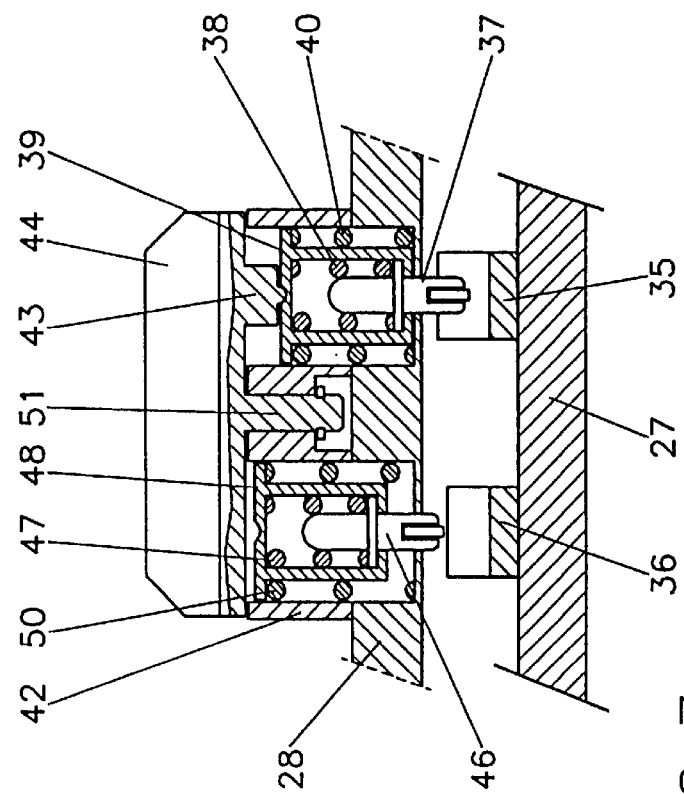
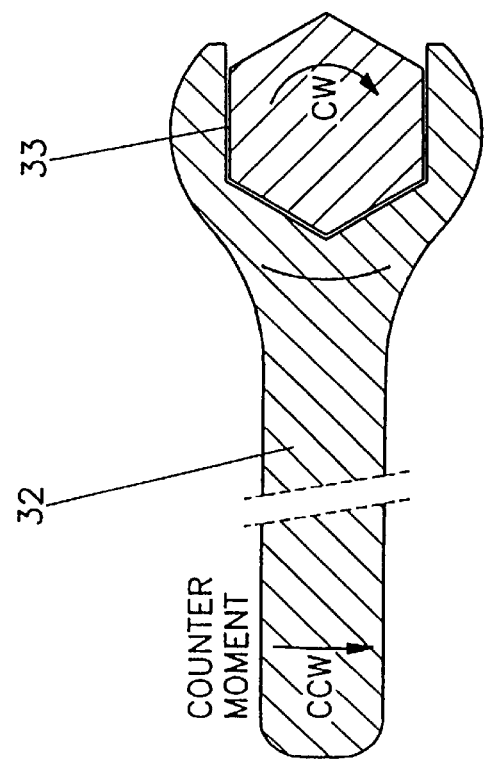
FIG.3
FIG.2

POWER TOOL

CROSS-REFERENCE TO RELATED APPLICATION

This is a continuation-in-part of U.S. patent application Ser. No. 08/473,880, filed Jun. 7, 1995, now U.S. Pat. No. 5,592,866, which is a continuation of U.S. patent application Ser. No. 08/100,949 filed Aug. 3, 1993, now U.S. Pat. No. 5,467,684, which is a continuation-in-part of U.S. patent application Ser. No. 08/083,760, filed Jun. 30, 1993, now U.S. Pat. No. 5,350,390, which is a continuation of U.S. patent application Ser. No. 07/857,556, filed Mar. 25, 1992, now abandoned.

BACKGROUND OF THE INVENTION

1. Technical Field

The present invention relates to the field of power tools, and more particularly to power screw-drivers, power wrenches, drills etc.

2. Discussion of the Prior Art

A rotary piston driving mechanism is described in U.S. Pat. No. 5,467,684 to Sher which is incorporated by reference in its entirety for all purposes as if fully set forth herein. In connection with FIG. 10 of that patent a mechanism is described in which a longitudinal reciprocating motion of a piston in a cylinder is transformed into a rotational motion of a working head. The mechanism utilizes a closed wave-shaped groove defined in either the cylinder or the piston. Guiding members are projecting into the groove. When the piston is forced to move longitudinally the groove slides over the guiding members to cause rotation. The working head is connected to the piston via a linear sliding element e.g., a spline, thus causing the working head to perform only a rotational motion.

Certain power tools are required to deliver sufficient torsional moment to enable tightening or releasing of a fastener such as a screw or a nut, and to be able to rotate the working head in two directions. One direction is for tightening and the other direction is for releasing the fastener. It is also desirable that the torsional moment can be adjusted to prevent overtorquing of the fastener. In cases where the power tool is used by an operator it is advantageous that the tool is small in size and has low weight.

Power tools are very common and widely in use. Power tools replace manually operated tools, especially in cases were the work volume or the force requirements are high e.g., a power screw-driver replaces a manual screw driver etc. Usually power tools are operated by pneumatic, hydraulic, electric line power, or by batteries.

The invention described herein can be used also as a drill.

It is to be understood that this invention can also be used in other areas e.g. surgical operation, and the like.

OBJECTS AND SUMMARY OF THE INVENTION

It is an object of the invention to provide an improved method and a power tool for tightening and releasing fasteners, specifically screws, nuts, bolts etc.,.

It is another object of the present invention to provide a power tool that can rotate a drill bit.

Still another object of the present invention is to provide a power tool that has a high ratio of power to size.

Still another object of the present invention is to provide a power tool that has a high ratio of power to weight.

A further object of the present invention is to provide a power tool that its driving unit can be separated from the working head for applications in hard-to-reach places.

It is also an object of the present invention to provide a power tool that can be operated via curved paths.

It is another object of the present invention to provide a tool that has high torsional moment even at low rotational speed.

Still another object of the present invention is to provide a power tool that the rotational speed of the working head can be changed.

A further object of the present invention is to provide a power tool in which the torsional moment can be adjusted to prevent overtorquing of the fastener.

It is also an object of the present invention to provide a tool that has a low level of noise.

It is another object of the present invention to provide a tool that has a low level of vibration.

Still another object of the present invention is to provide a system that includes a driving unit that can automatically operate and control the tool.

A further object of the present invention is to provide a power tool that can be operated manually.

It is also an object of the present invention to provide a power tool that has a simple design.

In accordance with the preferred embodiment of the present invention there is provided a power tool which utilizes a rotary piston driving mechanism. This mechanism enables movement of a working head in a rotational motion. The power tool is attached to a driving unit via two flexible tubes surrounded by a jacket or alternatively, via a multilumen tubing that contains two lumens. One of the tubes is used for transferring pressurized fluid for advancing the rotating piston in a forward direction and the second tube is used for moving the rotating piston in a backward direction. In the driving unit each tube is connected to a reciprocating piston. The two pistons are reciprocated in unison, that is when one piston moves in a forward direction the other one moves in a backward direction, and vice versa. The reciprocating motion of the pistons in the driving unit causes the pressure in the tubes to increase or decrease, thus operating the rotating piston. There are many ways to operate the pistons of the driving unit in a unison reciprocating motion. In one way, that is the preferred embodiment and is described later in details, each piston is connected to an electric linear actuator. An electronic controller operates the linear actuators in unison; thus, when one actuator is moving in a forward direction the second one moves in a backward direction and vice versa. The controller reverses the direction of the linear actuator according to pressure that it senses from a pressure transducer or according to the axial movement of the actuator that is sensed by an encoder. The controller has other functions as well, e.g., controlling the speed of the working head and adjusting the moment delivered to the working head in order to avoid overtorquing of the fastener. Another way to cause the two pistons to move in unison is by using a reciprocating mechanism. An example of a reciprocating mechanism is a rotating cam shaft that has two cams each located against one piston. It is also possible to use a crank shaft to cause the reciprocating movement of the pistons. The simplest way to reciprocate the pistons is by manual operation. This can be done by a lever that is connected to the two pistons. The lever is also connected to a pivot that is located midway between the two pistons. When the lever is operated manually in a reciprocating motion the pistons will also reciprocate.

It is obvious that in order to allow the tool to perform a useful work a moment that counters the moment exerted by the working head must be applied on the cylinder. Without the counter moment the whole tool will rotate about its longitudinal axis and no work can be performed. The counter moment can be applied directly by the operator's hand on the cylinder or, in cases where the moment is high, by using a wrench. There are cases where the power tool is used in places that cannot be reached by an operator hand or by a wrench, e.g., inside a pipe. In these cases the counter moment can be applied by other means e.g., gripping elements. Gripping elements such as gripping shoes that grip the side wall of the pipe are known, e.g., the gripping shoes described in U.S. Pat. No. 4,314,615 to Sodder et al. Another method that can serve for the same purpose is using an inflatable balloon that is mounted on the outside circumference of the cylinder. The balloon is deflated during the insertion in the pipe. When the working head is adjacent the fastener the balloon is inflated, thus fixing the cylinder against the wall of the pipe. It is clear that in order to operate the gripping element additional tubes must be added to the bundle. The operation of the gripping element can be controlled by the controller. The simplest way of applying a counter moment is by exploiting the tube that connects the tool to the driving unit. If the tube has a high enough torsional stiffness then the working head moment can be transferred to the driving unit that can counter this moment.

Another important requirement a power tool should fulfill is to be able to rotate in both directions, thereby enabling tightening or releasing of the fastener. The closed groove described in detail in U.S. Pat. No. 5,467,684 to Sher can have any shape. In the preferred embodiment the groove is designed in an axial symmetrical shape, meaning that the segments of the groove are equal. The reason for using this shape is to enable rotation of the working head in both directions. As a consequence of this design, when the guiding member or ball reaches the apex of the groove it has no preference in which direction to move. A mechanism that forces a rotation of the working head in a desired direction must be added to the tool. There are two ways to accomplish this goal. The first one is by exploiting the counter moment that was previously described. The counter moment is applied by the operator constantly. When the ball reaches the apex of the groove there is a momentarily pause in the rotation movement of the working head and the moment exerted by the working head is zeroed. The counter moment is used during this instance to force the ball over the apex of the groove. The end result is a unidirectional rotation of the working head. This type of operation is simple and intuitive.

A second method that serves only for the purpose of forcing the working head in a desired direction of rotation is by a bi-directional rotation mechanism. The bi-directional rotating mechanism is an assembly that is located within the tool and has two positions, one position for tightening and the other one for releasing the fastener.

It should be noted that the type of working head is not part of the invention and therefore is not described in details.

BRIEF DESCRIPTION OF THE DRAWINGS

The above and still further objects, features and advantages of the present invention will become apparent upon considering the following detailed description of specific embodiments thereof, particularly when viewed in conjunction with the accompanying drawings wherein like reference numerals in the various figures are utilized to designate like components.

FIG. 2 is a view in transverse section taken along lines 2—2 of FIG. 1.

FIG. 3 is a detailed view in longitudinal section of a portion of the distal end of the power tool of FIG. 1 and showing the bi-directional rotation mechanism of FIG. 1.

DESCRIPTION OF THE PREFERRED EMBODIMENTS

Figure 1:
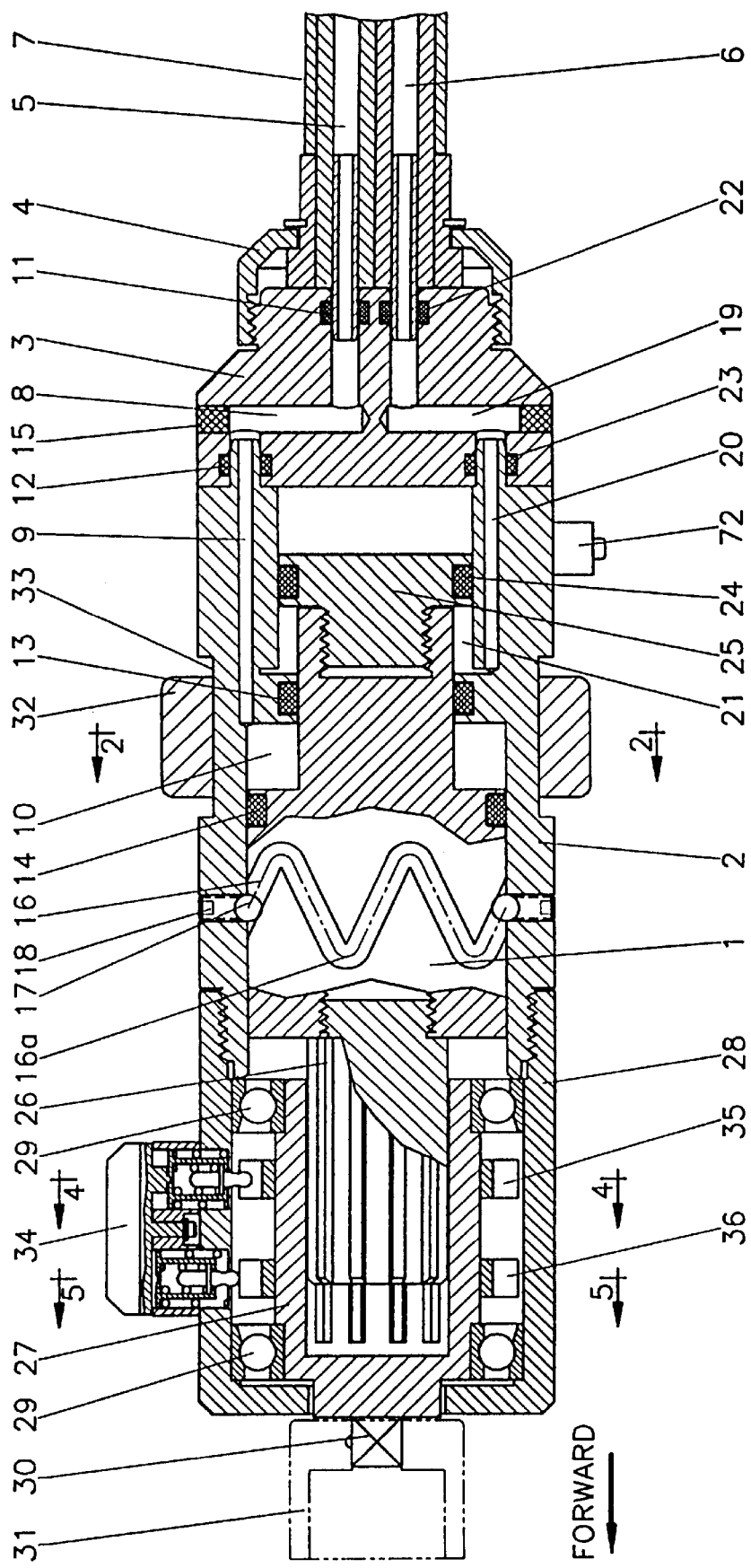
FIG. 1 is a view in longitudinal section of an embodiment of the power tool of the present invention.

An embodiment of the power tool is shown in FIG. 1. A piston 1 is located within cylinder 2. Cylinder 2 is closed by adapter 3. Adapter 3 is connected via a swivel connector 4, to a bundle of two tubes, tube 5 and tube 6. Tube 5 and tube 6 are located with a jacket 7. Tube 5 and tube 6 are connected to a driving unit described below. When pressure is applied to tube 5 it will be transferred via channel 8 and channel 9 to chamber 10. The pressure along this path is maintained by O-ring 11, O-ring 12, O-ring 13 and O-ring 14. Plug 15 is for manufacturing purposes only. The pressure in chamber 10 forces piston 1 to move in a forward or distal direction. Piston 1 contains a closed groove 16. One or more balls 17 located in cylinder 2 and secured with set screws 18 protrude into groove 16. Piston 1 while moving is also forced to rotate because groove 16 rides over ball 17. The end result is a combined forward longitudinal and rotary motion of piston 1. A similar combined longitudinal and rotation motion of piston I occurs when pressure is applied to tube 6, except that now the longitudinal motion is in a backward or proximal direction. The pressure in tube 6 is transferred to chamber 21 via channel 19 and channel 20. The pressure is maintained by O-ring 22, O-ring 23, O-ring 24 and O-ring 13. It should be noted that O-ring 24 is mounted on ring 25. Ring 25 is threaded to piston 1 in order to allow assembly of piston 1. When chamber 21 is pressurized piston 1 will move backward, but because groove 16 slides over ball 17, it will also rotate at the same time. It should be noted here that groove 16 is axially symmetrical. The direction in which ball 17 will proceed in the next segment of groove 16 is arbitrary because of the symmetrical structure of the groove 16. The reason for making the groove 16 symmetrical is to allow rotation of the working head in both directions, clockwise and counter clockwise. The way in which the working head is forced to rotate in a predetermined rotation is discussed below. A spline 26 is fixedly connected to piston 1. It should be noted that a spline 26 can be replaced by any other linear sliding element such as a ball spline, a key etc.,. Spline 26 linearly slides within spindle 27. Spindle 27 is mounted inside housing 28 with two bearings 29. Housing 28 is threaded to cylinder 2. Spindle 27 ends with a square drive 30 to which a working head 31 is attached. Working head 31 is shown in phantom lines as the specifics thereof do not, per se, constitutes part of this invention. The working head can be a screw driver bit, a socket, a drill etc.,. It was previously mentioned that piston 1 performs a combined longitudinal and rotational movement. Spline 26, being fixedly attached to piston 1, performs the same motion, but spindle 27 can only rotate because the longitudinal movement can not be transferred to spindle 27 by spline 26. The end result is that working head 31 performs only a rotational movement. It is clear that in order for working head 31 to perform a useful work a moment that counters the moment exerted by the working head must be applied on cylinder 2. Referring to FIG. 2, wrench 32 is attached to flats 33 on the external surface of cylinder 2. The counter moment is applied by the operator on wrench 32. Without applying this counter moment the whole tool will rotate about its longitudinal axis and will not perform any useful work.

It is to be noted that in cases where the moment is small, the operator can hold the cylinder with his hand instead of using a wrench. It is also clear that the wrench 32 can be replaced by a member that is an integral part of cylinder 2.

Two methods of forcing rotation in a desired direction are described. One method is by using wrench 32 that, as previously described, is used for giving the counter moment. The other one employs a bi-directional rotation mechanism that comprises of a changeover mechanism 34, a cw (clockwise) plate cam 35 and a ccw (counter clockwise) plate cam 36.

(Note: cw and ccw are referenced when looking in a forward or distal direction).

It is clear that in order to have a unidirectional rotation ball 17 must be forced to ride over and pass apex 16a (shown in FIG. 1) of groove 16. Subsequently, ball 17 will proceed to the adjacent segment of groove 16 and will not return to the segment of groove 16 that has been immediately traversed.

Referring again to FIG. 2. The operator must exert a ccw moment on cylinder 2 in order to counter the cw moment developed by the working head 31. However, when ball 17 reaches the apex 16a there is a momentary pause in the rotation of the working head and of piston 1 attached to it, and at this point the moment exerted by the working head is zeroed. The counter moment exerted by the operator at that momentary pause will cause the cylinder 2 and the ball 17 that are located in cylinder 2 to rotate ccw. The end result will be that ball 17 will pass apex 16a, and when piston 1 reverses its longitudinal direction the rotation will be cw. The rotation continues in the cw direction as long as the operator is exerting a moment in ccw direction. This type of operation is simple and intuitive.

There are situations where the counter moment is not exerted by an operator but rather by a fixed stop e.g. when the wrench is leaned against a fixed wall. In this case the counter moment is developed solely as a reaction to the moment developed by the working head. When the ball 17 reaches apex 16a, there is no moment to force it to pass apex 16a. For such cases a bi-directional rotation mechanism is suggested. The mechanism is illustrated in FIG. 1, FIG. 3, FIG. 4 and FIG. 5. The bi-directional rotation mechanism comprises: a change over mechanism 34 that is detailed in FIG. 3, a plate cam 35 shown in FIG. 4 and a plate cam 36 shown in FIG. 5.

Figure 4:
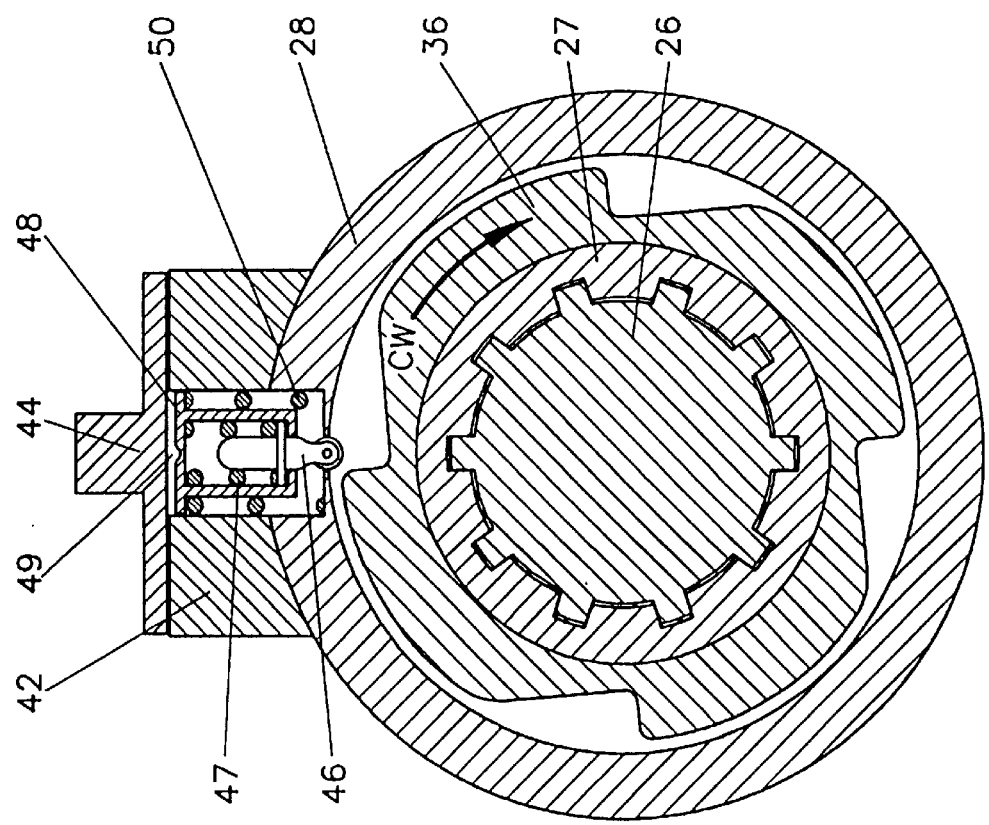
FIG. 4 is a view in transverse section taken along lines 4—4 of FIG. 1.

Referring to FIG. 3 and FIG. 4 plate cam 35 is fixedly attached to spindle 27. Plate cam 35 has four recesses comprising of slope 35a, that is moderately inclined, and slope 35b, that is steeply inclined. The number of recesses corresponds to the number of apices 16a of groove 16. A cam follower 37 rides over plate cam 35. Cam follower 37 is pushed against plate cam 35 by spring 38. Cam follower 37 and spring 38 are located in housing 39. This assembly of housing 39 including its internal parts is pushed radially outward in opening 41 located in housing 42 by spring 40. Housing 39 can move outward until it encounters protrusion 43 that is a part of change-over knob 44. In the position shown in FIG. 3 and FIG. 4 cam follower 37 is always in contact with plate cam 35. As the plate cam 35 rotates in cw direction cam follower 37 will move outward while riding over slope 35a until it encounters slope 35b of the adjacent recess. At this point cam follower 37 will move radially inward and by doing so it will push plate cam 35 in a cw direction. It was mentioned before that the recesses in plate cam 35 correspond to the apices 16a of groove 16. More specifically, slope 35b is located exactly against the apex 16a. Thus when slope 35b is pushed by cam follower 37 in cw direction, ball 17 pass over the apices into the next adjacent segment of groove 16. This situation repeats itself at every recess and the end result is a unidirectional rotation.

Figure 5:
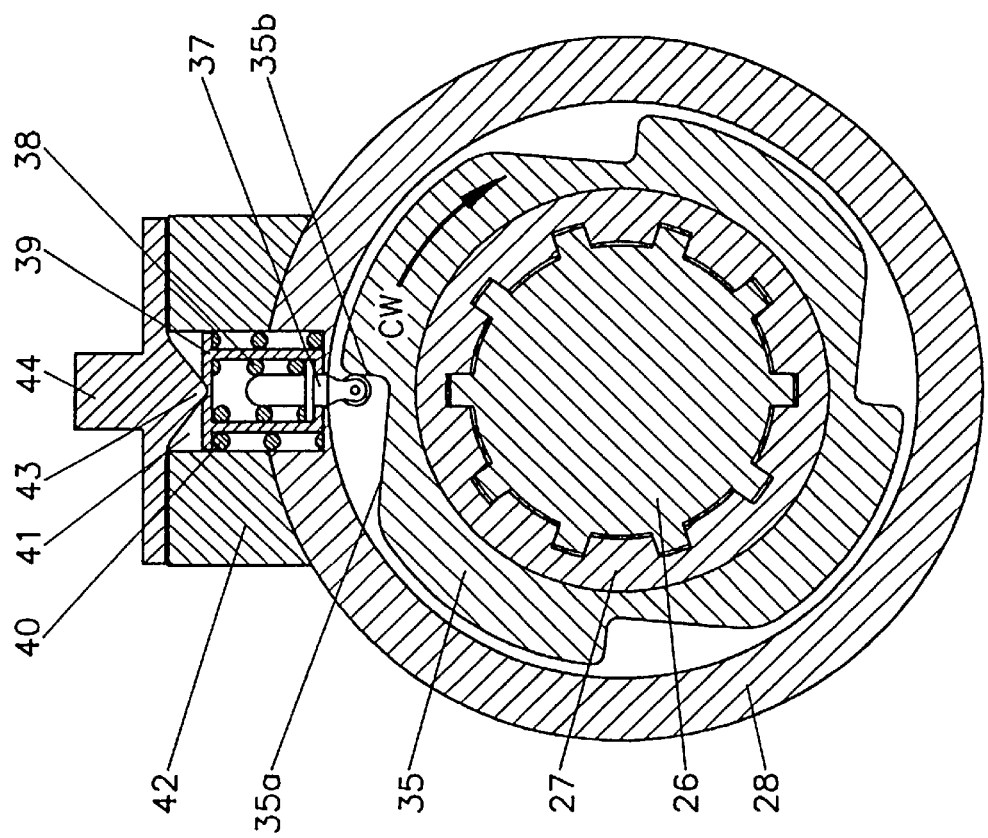
FIG. 5 is a view in transverse section taken along lines 5—5 of FIG. 1.

Referring to FIG. 3 and FIG. 5, a second plate cam 36 is fixedly attached to spindle 27. Plate cam 36 is used for the ccw rotation of the working head. The situation depicted in FIG. 3 and FIG. 5 shows follower cam 46 in an idle position. Cam follower 46 is pushed radially inward by spring 47. Cam follower 46 and spring 47 are located in housing 48. This assembly of housing 48 including its internal parts is pushed radially outward by spring 50 in opening 49 located in housing 42. Housing 48 can move outward until it encounters change-over knob 44. The difference in the position of housing 48 vs. housing 39 is that housing 48 can move further outward. In the position shown in FIG. 3 and FIG. 5 cam follower 46 does not touch plate cam 36.

In order to change the direction of rotation of the working head, change-over knob 44 must be rotated 180 degrees. The rotation is done by rotating knob 44 on pivot 51 (shown in FIG. 3). When knob 44 is rotated, protrusion 43 will push housing 48 inward while housing 39 will move outward. The previous discussion is applicable to this case, as well, except that now the working head rotates in a ccw rotation.

Figure 6:
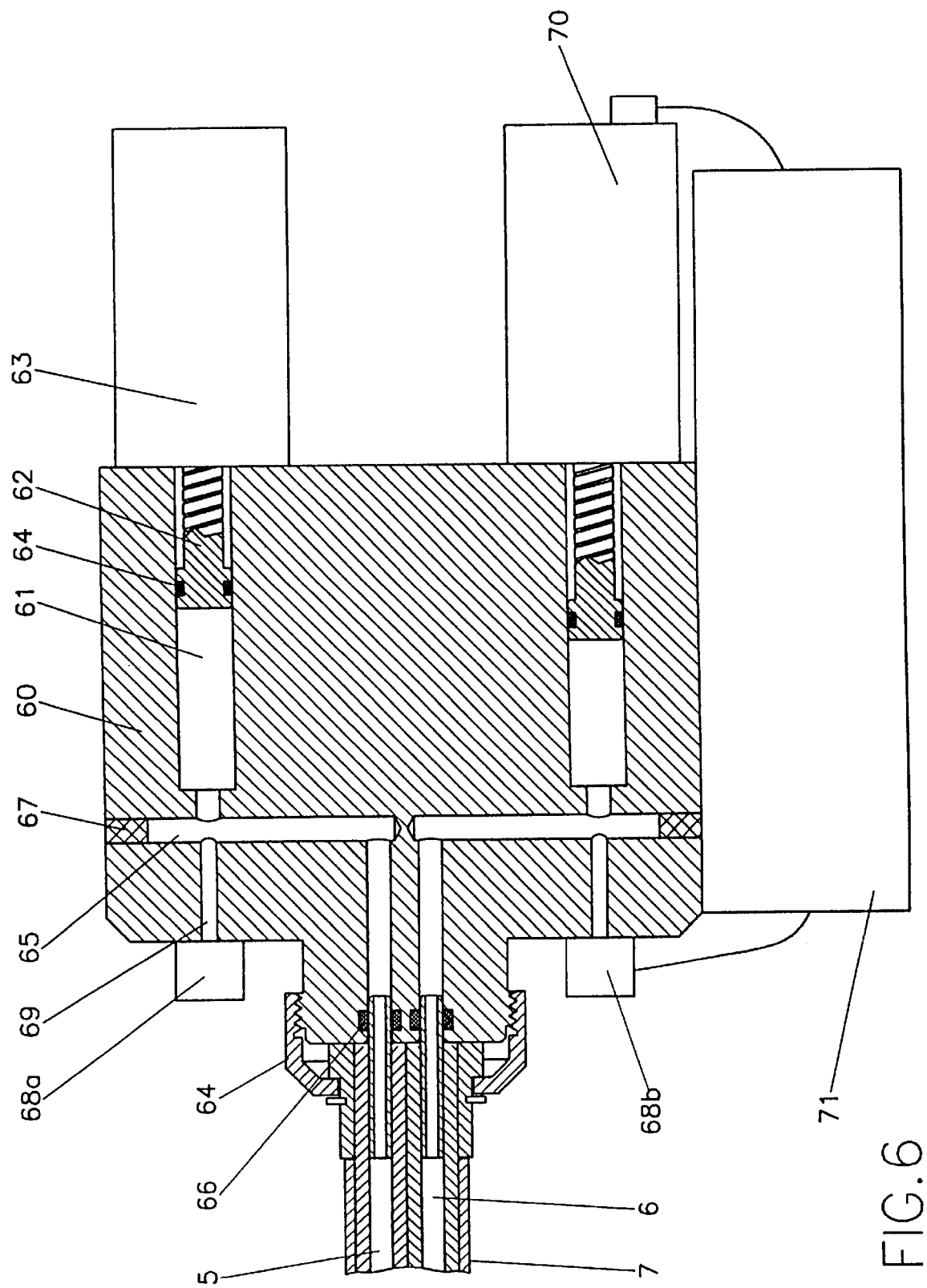
FIG. 6 is a view in longitudinal section of an embodiment of the driving unit located at the proximal end of the power tool of FIG. 1.

FIG. 6 describes an embodiment of the driving unit. The role of driving unit is to supply pressure to the power tool. The driving unit comprises a housing 60 in which two bores 61 are located. Piston 62 is located inside bore 61. Piston 62 is fixedly attached to an electric linear actuator 63. Operation of linear actuator 63 either increases or decreases the pressure in bore 61. A swivel connector 64, connects between housing 60 and a bundle of two tubes, tube 5 and tube 6. Tube 5 and tube 6 are located within a jacket 7. Tube 5 and tube 6 are connected to the power tool in a way that was described previously. Increasing the pressure in tube 5 will cause piston 1 to move forward. The pressure is transferred from bore 61 to tube 5 via channel 65. Pressure is maintained with O-ring 64 and O-ring 66. Plug 67 closes channel 65 and is used for manufacturing reasons. It was previously described that the pressure in tube 5 pushes piston 1 forward. A pressure sensor 68a is connected to channel 65 via channel 69, thus sensing the pressure in tube 5. The preceding description is applicable also for tube 6. Linear actuator 70 causes changes of pressure in tube 6. This pressure is sensed by pressure sensor 68b. It was described earlier that when tube 6 is pressurized piston 1 moves backward.

The operation of the power tool is controlled by electronic controller 71. The linear actuators 63 and 70, the pressure sensors 68a and 68b and on/off switch 72 (shown in FIG. 1) are electrically connected to the controller 71. The operation of the power tool starts when switch 72 is switched on by the operator. The controller operates actuators 63 and 70 in unison. Thus when the pressure in tube 5 increases, the pressure in tube 6 decreases and vice versa. The controller changes directions of movement of actuators 63 and 70 according to the pressure that is sensed by pressure sensors 68a and 68b. Alternatively, the controller can be programmed to change directions by sensing the linear movement done by the actuators. Another important function of the controller is its ability to control the pressure that gives rise to a simple of adjusting the torsional moment in order to prevent overtorquing of the fastener. An additional function of the controller is to change the rotational speed of the working head.

It is to be understood that the power tool described in this invention contains features that are not required for some applications. For example, there are cases where there is no need for the bi-directional rotation mechanism. In other cases where the load is light there is no need for a wrench.

It is to be understood that in order to reduce the stresses on balls 17, two or more closed groove 16, spaced longitudinally on piston 1 can be used.

It is also to be understood that the linear actuator may be hydraulic or pneumatic.

Having described the preferred embodiment, it is believed that other modifications, variations and changes will be suggested by persons skilled in the art in view of the teaching set forth herein. It is therefore to be understood that all such variations, modifications and changes fall within the scope of the present invention as defined by the appended claims.

What is claimed is:

1. A power tool for driving fasteners and for drilling purposes, said power tool comprising:
   (a) a housing;
   (b) a piston slidable within said housing;
   (c) a rotary piston driving mechanism for converting longitudinal motion of said piston in said housing to a combined longitudinal and rotary movement of said piston;
   (d) a linear sliding element for converting said combined longitudinal and rotary movement of said piston into a rotation movement;
   (e) a working head fixedly attached to said linear sliding element; and
   (f) a counter moment element attached to said housing.

2. The power tool of claim 1, further comprising a driving unit for driving said rotary piston.

3. The power tool of claim 2, wherein said driving unit comprises linear actuators, and a controller for operating said actuators.

4. The power tool of claim 2, wherein said driving unit comprises a reciprocating mechanism.

5. The power tool of claim 2, wherein said driving unit is manually operated.

6. The power tool of claim 1, further comprising a bundle for connecting said rotary piston to said driving unit.

7. The power tool of claim 1, wherein said counter moment element is applied directly by the operator's hand on said housing.

8. The power tool of claim 1, wherein said counter moment element is a wrench connected to said housing.

9. The power tool of claim 1, wherein said counter moment element is an integral part of said housing.

10. The power tool of claim 1, wherein said counter moment is applied by said bundle.

11. The power tool of claim 1, wherein said counter moment element is a gripping element connected to said housing.

12. The power tool of claim 1, further comprising a bi-directional rotation mechanism.

13. The power tool of claim 1, wherein said rotary piston driving mechanism includes:
   (i) one or more endless guide grooves defined in one of said piston and said housing and each comprising a series of groove sections of generally alternating directions; and
   (ii) motion conversion means responsive to linear motion of said piston in said housing for causing said piston to rotate relative to said housing about said axis, said motion conversion means including at least one guide member secured in the other of said piston and said housing and projecting substantially radially and into said guide grooves.

14. The power tool of claim 13 wherein each of said groove sections has a constant slope throughout substantially all of its length between successive apices.

* * * * *